US006277415B1

(12) United States Patent
Levin et al.

(10) Patent No.: US 6,277,415 B1
(45) Date of Patent: *Aug. 21, 2001

(54) PEDICULOCIDAL AND VETERINARY COMPOSITIONS

(76) Inventors: Orna Levin, P.O. Box 3561, Kfar Neter 40593; David Marcos, Kibbutz Maabarot, 40230, both of (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,082

(22) Filed: Oct. 13, 1999

Related U.S. Application Data

(63) Continuation-in-part of application No. 08/625,495, filed on Mar. 29, 1996.

(51) Int. Cl.$^7$ .......................... A01N 65/00; A01N 25/00; A61K 35/78; A61K 39/385
(52) U.S. Cl. .......................... 424/725; 424/405; 424/757; 424/764
(58) Field of Search ................... 424/195.1, 401, 424/405, 522, 114, 725, 757, 764; 510/119, 109; 514/881

(56) References Cited

FOREIGN PATENT DOCUMENTS

2197413 * 9/1997 (CA) ............................... A61K/9/06

OTHER PUBLICATIONS

Natural Insecticide Spray Against Lice; Israel Faxx, vol. 4, No. 129 (Abstract), Jul. 1996.*

Eder, R. Looking for the Next Big Winner At Progressive Natural Products Expo.; Drug Store News, vol. 21, No. 7, pp. 30(1), Jul. 1996.*

* cited by examiner

Primary Examiner—Jon P. Weber
Assistant Examiner—Patricia D Patten
(74) Attorney, Agent, or Firm—Mark M. Friedman

(57) ABSTRACT

A pharmaceutical or veterinary composition which includes one or more volatile oil, one or more alcohol and one or more fixed oil and/or one or more emollient ester of fatty acid derived from vegetable oils.

23 Claims, No Drawings

PEDICULOCIDAL AND VETERINARY COMPOSITIONS

This application is a CIP of 08/625,495 filed Mar. 29, 1996.

FIELD AND BACKGROUND OF THE INVENTION

The present invention relates to a pediculocidal composition. More particularly, the present invention is of compositions which contain anise oil as at least one of the active ingredients and which have unexpectedly significant activity against lice.

Volatile oils are well known in the art for the treatment of medical problems. For example, these oils have been used in folk medicine, natural therapy, aromatherapy and even in traditional (Western) medicine. Volatile oils in connection with the present invention are those essential oils embraced by the definition in Hackh's Chemical Dictionary, 4th Edition, page 248.

A number of volatile oils found in plants are known to repel or kill insects. The volatile oils might be part of the mechanisms which plants use to protect themselves from attack by insects and animals. This property to kill or repel insects has also been exploited to produce various medicines. For example, the use of volatile oils in the treatment of parasitic infestations is described in "The Manual of Natural Therapy" by M. Olshevsky, B. Noy and M. Zwang (Published by Facts of Life, New York, 1989). For scabies, the following treatment is suggested (pp 183, 185): "Use the essence of geranium 5% in olive oil base and massage the affected part of the skin once per day until condition improves." For lice, the following is suggested (P. 185): "Rub the whole body with the following combination in olive oil base: crushed garlic 10%, lavender essence 3%, thyme 2%, rosemary 4%. Do this treatment once per day until condition improves."

Lice belong to the group of external parasites living on warm blooded animals. In humans, lice are responsible for pediculosis, a parasitic infestation of the skin, trunk or pubic areas. There are three different varieties: (1) Pediculosis pubis caused by *Pithirus pubis;* (2) *Pediculosis corporis,* caused by *Pediculus humanus* humanus; and (3) Pediculosis capits, caused by *Pediculus humanis* capatis.

Scabies is a common type of dermatitis, or irritation of the skin, caused by infestation with the mite *Sarcoptes scabisi.* This skin disease affects humans and is also found in various forms in animals such as dogs, cattle, sheep, camels and birds.

Both scabies and pediculosis are conditions which affect millions of humans world-wide. A variety of treatments are known in the art for scabies or lice infestations but none has succeeded in eradicating these two conditions. Epidemics of scabies and of pediculosis appear to be cyclical in nature.

Although certain volatile oils, such as rosemary oil, have been suggested as treatments, these volatile oils have a number of drawbacks. First, the volatile oils are rather expensive. Moreover, the traditional way to use pure volatile oils, by direct application of the pure oil to the skin, frequently causes skin irritation, accompanied by a burning sensation and erythema, when applied to the skin. Diluting the volatile oils in a fixed oil such as olive oil may reduce these side-effects but also reduces their potency. The resultant treatment is less effective and often requires repeated applications. Fixed oils in connection with the present invention are those embraced by the definition in Hackh's Dictionary (Chemical). 4th Edition, page 269. Dissolving a volatile oil in an alcohol, e.g. ethanol, retains the anti-insect properties but also retains the undesired side-effects, e.g., the burning sensation on the skin and erythema.

Furthermore, the background art neither teaches nor suggests a composition which includes anise as at least one of the active ingredients and which also includes an alcohol and a vegetable oil or other suitable type of fixed oil. Certainly, the background art neither teaches nor suggests such a composition for the treatment of lice. For example, United Kingdom Patent Application No. 2,228,411 teaches a cosmetic composition for application to the skin, which includes ethyl alcohol and vegetable oil, and which may optionally include rosemary essential oil. However, United Kingdom Patent Application No. 2,228,411 neither teaches nor suggests anise oil as a suitable ingredient for this cosmetic composition.

Similarly, U.S. Pat. No. 5,455,055 teaches a composition which includes vegetable oil, ethyl alcohol and an herbal extract, but neither teaches nor suggests anise oil as a suitable type of herbal extract. In any case, the taught composition is a salad dressing spray foodstuff and is not taught to have any type of activity against lice.

United Kingdom Patent Application No. 1,574,609 teaches a pesticidal composition, but neither teaches nor suggests anise oil as a suitable ingredient for this composition.

It has therefore been desirable to find a pharmaceutical or veterinary composition which has the desired anti-insect properties, in which a lower concentration of volatile oils may be used, particularly the volatile oil anise oil, and which has no adverse effect on the skin.

SUMMARY OF THE INVENTION

The compositions and methods of the present invention are directed toward the treatment of lice. The composition includes at least one volatile oil, preferably anise oil; at least one alcohol; and at least one fixed oil and/or one or more emollient ester of fatty acid derived from vegetable oils. The composition according to the present invention is preferably a solution and is prepared by admixing the various ingredients. Suitable volatile oils are, e.g., anise oil, calendula oil, quassia oil, rosemary oil and Sassafras oil. Suitable alcohols are, e.g., ethanol and isopropyl alcohol. Suitable fixed oils are, e.g., almond oil, avocado oil, maize oil, olive oil, peanut oil, soya oil, sunflower oil, sesame seed oil, safflower oil and fractionated coconut oil. Suitable esters include but are not limited to medium chain triglycerides (MCT), caprylic/capric triglyceride; isopropyl myristate; propylene glycol dicaprylate—dicaprate; and isopropyl palmitate. MCT are e.g. those as defined in German Pharmacopea, 8th Edition. Most preferably, such a vegetable oil is olive oil.

According to preferred embodiments of the present invention, the composition includes anise oil at a concentration in a range of from about 5% to about 40%, and more preferably from about 15% to about 30%, volume per volume; isopropyl alcohol present at a concentration in a range of from about 20% to about 60% volume per volume; and at least one ingredient selected from the group consisting of fixed oil and emollient ester of fatty acid derived from vegetable oils, which is most preferably coconut oil. More preferably, the composition also includes rosemary oil, most preferably at a concentration in a range of from about 5% to about 25%. Also more preferably, the composition also includes sassafras oil, most preferably at a concentration in a range of from about 5% to about 25%.

The composition of the present invention is preferably applied topically to the subject, more preferably to the skin and hair of the subject. The subject may be human or lower mammal. According to preferred embodiments of the present invention, the treatment with the composition of the present invention is used to kill eggs of the lice, as well as to kill the lice themselves. Such a treatment may also be used to repel the lice from the head of the subject, as described in greater detail below.

DESCRIPTION OF THE PREFERRED EMBODIMENTS

The compositions of the present invention feature a synergistic mixture of anise oil, a fixed oil which is preferably coconut oil and an alcohol which is preferably isopropyl alcohol. Optionally and preferably, the mixture also includes rosemary oil. This mixture has unexpectedly great efficacy against lice, including both lice eggs and the hatched lice form, when topically applied to a subject infested with lice. Furthermore, the composition of the present invention overcomes deficiencies in background art treatments for lice in that the ingredients of this composition are non-toxic and are not irritating to the skin. By contrast, many commercial formulations use highly toxic chemicals and/or are ineffective against lice in one or both forms. Thus, the present invention overcomes the known deficiencies of the background art formulations.

(Whatman No. 2) and exposed to 1 g of the test formulation. The lice were left in contact with the formulation for 15 minutes. Thereafter they were removed and shampooed for one minute with a regular shampoo and then washed for one minute under running tap water. After treatment the lice were transferred to a fresh filter paper disc and incubated overnight at optimum temperatures and humidifies. Mortality was determined after 24 hours.

In order to examine the ovicidal activity lice were allowed to oviposition human hair. Fifty 2–6 day old eggs were tested according to the same procedure as for lice. Mortality count was made after 10 days. The testing for lice and eggs was repeated 3 times. The results are shown in Table 1.

The tested formulations are described in Table 1. In addition, two commercially available formulations, designated as E606/90G and E606/90H, were also tested (Hafif and Kin-X spray, respectively, both available from Abic). The results of the experiments are shown in Table 2.

TABLE 1

Tested Formulations

| Formulation | olive oil | anise oil | rosemary oil | ethanol (95%) | sassafras oil | estasan GTB-60 | isopropanol |
|---|---|---|---|---|---|---|---|
| E606/90A | 20 | 15 | 15 | 0 | 0 | 27.9 | 30 |
| E606/90C | 0 | 13.2 | 3.7 | 27.9 | 13.2 | 27.9 | 14 |
| E606/90I | 25 | 10 | 10 | 0 | 0 | 25 | 30 |
| E637/90A | 40 | 15 | 5 | 0 | 0 | 0 | 40 |
| E637/90C | 10 | 15 | 5 | 35 | 0 | 30 | 5 |
| E757/91A | 0 | 0 | 0 | 0 | 0 | 100 | 0 |
| E757/91D | 0 | 15 | 0 | 0 | 0 | 45 | 40 |
| E757/91E | 0 | 15 | 5 | 0 | 0 | 40 | 40 |
| ALA | 0 | 33 | 0 | 67 | 0 | 0 | 0 |
| ALR | 0 | 0 | 33 | 67 | 0 | 0 | 0 |
| E565/89A | 0 | 27.8 | 5.5 | 66.7 | 0 | 0 | 0 |
| E565/89B | 0 | 5.5 | 27.8 | 66.7 | 0 | 0 | 0 |
| E565/89C | 0 | 16.7 | 66.7 | 0 | 0 | 0 | 0 |
| OOR | 33.3 | 33.3 | 33.3 | 0 | 0 | 0 | 0 |
| AL15AR | 0 | 15 | 15 | 70 | 70 | 70 | 70 |
| AL5AR | 0 | 5 | 25 | 70 | 70 | 70 | 70 |
| ALA5R | 0 | 25 | 5 | 70 | 70 | 70 | 70 |

EXAMPLE 1

Efficacy of Formulations of the Present Invention Against Lice

The pediculicidal activity of various formations was tested in the laboratory on human body louse *Pediclus humanus hunanus* according to the following methods:

Body lice were reared in the laboratory by feeding them every second day on rabbits. Lice were placed on the shaved abdomen of a white rabbit and left until they fed to satisfy. Outside the host the lice were maintained at a temperature of 30±1° C. and relative humidity of 70±10%.

For each test 50 lice (10 males, 10 females and 30 nymphs) were placed on a 7 cm white filter paper disc

TABLE 2

Results of Tests

| Formulation | Average % Mortality of Lice After 24 hours | Average % Mortality of Eggs After 10 Days |
|---|---|---|
| E606/90A | 100 | 17.2 |
| E606/90C | 98.7 | 21 |
| E606/90I | 94 | 11.4 |
| E637/90A | 100 | 26.5 |
| E637/90C | 97.3 | 40.6 |
| E757/91A | 46.7 | 57.6 |
| E757/91D | 100 | 59.6 |
| E757/91E | 99.3 | 56.8 |
| ALA | 100 | 72 |
| ALR | 100 | 42 |
| OOR | 100 | 18 |
| AL5AR | 100 | 61.1 |

TABLE 2-continued

Results of Tests

| Formulation | Average % Mortality of Lice After 24 hours | Average % Mortality of Eggs After 10 Days |
|---|---|---|
| AL15AR | 100 | 76.3 |
| ALA5R | 100 | 88.9 |

CONTROLS

| | Average % Mortality of Lice After 24 hours | Average % Mortality of Eggs After 10 Days |
|---|---|---|
| Positive Control Formulation | | |
| E606/90G | — | 6 |
| E606/90H | — | 13.3 |
| Negative Control Formulation | | |
| 40% ethanol | 8 | 6 |
| normal shampoo | 10.6 | 20.8 |

The MCT (medium chain triglyceride) utilized was Estasan™ manufactured by OS Industries APS, Copenhagen. Some of these preparations were tried on human volunteers and they did not cause the burning sensation or reddening of the skin associated with high concentration of volatile oils.

According to one particularly preferred embodiment of the present invention, the composition of the present invention includes: Fractionated Coconut oil (44%), Anise oil (15%), Isopropyl alcohol (40%) and 1% ylang ylang oil. The ylang ylang oil is added as a perfume, rather than as an active ingredient (as shown below, ylang ylang oil alone had no significant effect on lice). It should be noted that fractionated coconut oil is an example of the ingredient selected from the group consisting of fixed oil and emollient ester of fatty acid derived from vegetable oils of the present invention.

The efficacy of each of the ingredients of the preferred formulation of the composition of the present invention was tested both separately and as part of the composition itself As shown in the experimental data below, the composition of the present invention was clearly effective against lice, both in vitro and in vivo. Such efficacy is unexpected, and was not taught or suggested by the prior art.

The pediculicidal activity of the ingredients of this particularly preferred composition of the present invention was tested on the human body louse according to the following procedures. Body lice (*Pediculus humanus* humanus) were reared in the laboratory according to the method described by Cole (Cole, M. M. 1966, "Body lice", Insect colonisation and mass production, Smith, CNN. (ed.), Academic Press, N. York, p. 15–24). For each test 50 lice (10 males, 10 females and 30 nymphs) were placed on a 7 cm white filter paper disc and exposed to 1 ml. of the composition of the present invention or of the individual ingredients. The coconut oil, anise oil, and ylang ylang oil were first diluted in isopropyl alcohol before use.

The lice were left in contact with the substance for 15 min. They were removed from the test solution and washed with normal shampoo for 1 min and then with tap water for 1 min. After treatment lice were transferred to a fresh filter paper disc and incubated overnight at optimum temperature and humidity. Mortality was determined after 24 hours. Each experiment was conducted in triplicate. As a negative control 40% ethyl alcohol was used. The results of the tests can be seen in Table 3 below.

TABLE 3

Pediculicidal activity of the composition of the present invention after 15 min. of exposure.

| Ingredient | % morality of lice |
|---|---|
| Entire Composition | 100.0 |
| Fractionated Coconut oil (44%) | 83.3 |
| Anise oil (15%) | 91.3 |
| ylang ylang oil (1%) | 4.0 |
| Isopropyl alcohol (40%) | 2.7 |
| or Ethyl alcohol (40%) | 2.7 |

Lice which came in contact with entire composition, anise oil or coconut oil were either dead immediately after treatment or they were moribund, showing tremor and uncoordinated movements, which could be the result of a neurotoxic effect, similar to that seen in pyrethroid treated lice.

Next, the ovicidal activity of the ingredients of the composition of the present invention was tested on the human body louse according to the following procedure. Body lice were reared as described above. Lice were placed on human hair and left for 48 hrs. for oviposition. For each test, 50 eggs, 2–6 days-old, were placed on a 7 cm white filter paper disc and exposed to 1 ml. of the test formulation. The eggs were left in contact with the substance for 15 min. They were removed from the test solution and washed with normal shampoo for 1 min. and then with tap water for 1 min. After treatment eggs were transferred to a fresh filter paper disc and incubated at optimum temperature and humidity. Mortality was determined after 10 days.

The individual ingredients were prepared as described above. Each experiment was conducted in triplicate. As a negative control 40% ethyl alcohol was used. The results of the test can be seen in Table 4 below.

TABLE 4

Ovicidal activity of the ingredients of the composition of the present invention after 15 min. of exposure.

| Ingredient | % morality of lice |
|---|---|
| Entire Composition | 52.0 |
| Fractionated Coconut oil (44%) | 14.7 |
| Anise oil (15%) | 96.0 |
| ylang ylang oil (1%) | 11.3 |
| Isopropyl alcohol (40%) | 11.3 |
| or Ethyl alcohol (40%) | 8.0 |

Clearly, anise oil alone had a significant effect on the mortality of the lice while still in the egg stage, as did the entire composition.

In addition, in vivo studies were performed as a clinical trial with children infected with head lice, clearly demonstrating both the efficacy and safety of the composition of the present invention. These studies were performed with children from an area in the southern United States of America, which had had a significant problem with head lice. The problem was compounded by the fact that the previously effective products for treating head lice had ceased to be effective. The Health Department in this area was recommending treatment with the food product margarine as a "last resort" method. Health Department surveys indicated that some children had missed up to 60 days of school a year due to head lice infection.

Informational letters and informed consents (in English and Spanish) for the clinical trial and treatment program with the composition of the present invention were sent home with students before the trial began.

One elementary school was selected by the Health Department to participate in the school-based pilot program for head lice treatment using a composition of the present invention. All of the school's 520 students were screened by a professional grooming service. Those students identified with live lice or viable nits (lice eggs) were eligible to be included in the program. The parent/legal guardian of every participant signed an informed consent prior to treatment. The informed consent stated that the purpose of this pilot program was to: (a) assess the efficacy of the composition in killing head lice, and (b) test the feasibility of a school based head lice eradication program. All parents of children identified with active lice consented to their child's participation.

Once informed consents were obtained for eligible participants, demographic information (age, weight, and height), as well as participant member, hair length and texture was recorded for each participant. Each participant was treated with the composition for 15 minutes, rinsed off, and shampooed with a baby shampoo. As the composition was being rinsed, the rinse water was collected in a dishpan, and strained through a white towel to count the lice that came off the hair. This method was used to estimate the severity of the infestation prior to treatment. Seven days after the first treatment, participants returned for the one-week follow-up and second treatment. Prior to treatment, qualified health personnel thoroughly examined the head of each student for viable nits and live lice, which were counted and recorded. Students were then treated as before. Seven days later, participants returned for the two-week final follow-up. At this time, the hair and scalp of the participants were examined for live lice and viable nits. When live lice were found, the number and stage of development of live lice was also recorded.

Thirty-seven individuals, four males and 33 females, from 5 to 11 years of age were entered into the program. Thirty-two participants returned for the one-week follow-up and second treatment. Of the 32 participants who showed up for the second visit, 22 (68.8%) were free of lice. Of the ten with lice, eight had only nymphs, indicating hatching nits in the last week (poor ovicidal activity), and two had nymphs and one or two adults, probably indicating hatched nits and re-infestation from playmates or family members (see Table 5 below). The sibling of a program participant was included at this time when he was found to have a severe infestation.

Thirty participants returned for the final evaluation (this number includes the added sibling). Of these, 29 (96.7%) were lice free. Only one participant had a live louse, probably due to reinfestation from family members or the home environment. The second treatment was administered at the two-week follow-up. Thus, from these results, the composition after being applied for 15 minutes to dry hair demonstrated 93.8% pediculicidal activity. At the one-week follow-up, eight of 32 individuals (25%) in the program had nymphs hatched out from eggs that survived treatment. Two individuals with lice at all stages were found to have infested siblings or parents who had not been treated. Infested siblings and/or parents who were not treated were contacted and were either treated or given products to be applied at home. At two weeks, 29 of 30 volunteers (96.7%) were lice free. One individual had one adult louse and was determined to have been reinfested.

EXAMPLE 2

Efficacy of Formulations of the Present Invention as Repellents Against Lice

The formulations of the present invention were tested for their ability to repel human lice (*Pediculus humanus humanus*). The ability to repel lice is important as a preventative measure, given that many cases of lice arise from periodic outbreaks of infestations in groups of school-age children. Thus, those formulations of the present invention which are able to repel lice could be topically administered to school-age children when such an outbreak begins, thereby preventing the lice infestation from spreading to the treated children and obviating the need for additional treatments.

The formulations of the present invention which were tested for their ability to repel lice are designated as E767/91 A–H and are given in Table 5.

TABLE 5

| | Quantity in ml | | | | | | | |
|---|---|---|---|---|---|---|---|---|
| Ingredients | A | B | C | D | E | F | G | H |
| rosemary oil | — | — | — | — | 2.5 | 7.5 | 2.5 | — |
| anise oil | — | — | 2.5 | 7.5 | — | — | 7.5 | — |
| isopropanol | — | 20 | 20 | 20 | 20 | 20 | 20 | 120 |
| Estrasan | 50 | 30 | 27.5 | 22.5 | 27.5 | 22.5 | 20 | 174 |
| perfume (ylang) | — | — | — | — | — | — | — | 6 |

The experimental method was performed as follows. Body lice were reared in the laboratory by feeding them every second day on rabbits. Lice were placed on the shaved abdomen of a white rabbit and left until they fed to satisfaction. Outside the host the lice were maintained at a temperature of 30±1° C. and relative humidity of 70±10%. For each experiment, 20 female lice were used, which had been fed for 24 hours prior to the experiment.

The petri dish method was used to examine the repellency of the solutions for lice. Whatman 4 filter paper discs (5.5 cm diameter) were placed on petri dishes. Either 25 microliters or 100 microliters of the formulation of the present invention was then placed on a corduroy patch (1.5 cm$^2$). The material was allowed to dry in the incubator at 35° C. and 85–90% relative humidity. Control patches, containing a vehicle of the formulation of the present invention as a control solution or else absolute ethanol alone, were otherwise treated similarly. The patches were placed at the periphery of the filter paper at a maximnum separation from each other.

Twenty female lice were placed in the middle of the filter paper and the petri dish, together with the lice, was covered with a dark box in order to avoid any influence by light. The number of lice found on the treated and control patches was recorded after ten minutes. Each formulation was tested three times; results are given as an average percentage of repellency. As a negative control, a solution without the active ingredients, or alternatively absolute ethanol alone, was used. As a positive control, concentrated rosemary oil was used. The experiment was repeated 1, 3, 5, 7, 24 and 48 hours after the initial treatment of the patches.

The repellency was calculated according to the following equation:

$$\% \text{ Repellency} = 0.5A - n/0.5\,A \times 100$$

in which A is the total number of lice and n is the mean number of lice found in the treated patch. According to this equation, when lice are evenly distributed between the treated and untreated patches (n=0.5A), the percentage of repellency is close to zero, and when no lice are left on the treated patch, then repellency is 100%.

Table 6 below shows the repellency of the formulations of the present invention when compared to absolute ethanol, and Table 7 shows the repellency of the formulations of the present invention when compared to vehicle of the formulation. For Table 6, the quantity of each solution is 100 microliters, and for Table 7, the quantity of each solution is 25 microliters.

TABLE 6

| Formulations | Time after Exposure | Mean % Repellency |
| --- | --- | --- |
| A | 1 | 92.6 |
| B |   | 26.7 |
| C |   | 100 |
| D |   | 100 |
| E |   | 100 |
| F |   | 100 |
| G |   | 96.1 |
| H |   | 95.6 |
| C | 3 | 100 |
| D |   | 100 |
| E |   | 100 |
| G |   | 100 |
| C | 5 | 100 |
| D |   | 100 |
| E |   | 63.4 |
| G |   | 100 |

TABLE 7

| Formulations | Time after Exposure | Mean % Repellency |
| --- | --- | --- |
| G | 1 | 90 |
|   | 3 | 91 |
|   | 5 | 100 |
|   | 7 | 82.5 |
|   | 24 | 54.4 |
|   | 48 | 42 |
| D | 1 | 95.7 |
|   | 3 | 100 |
|   | 5 | 95.3 |
|   | 7 | 52.1 |
|   | 24 | 51.9 |
|   | 48 | 22.2 |
| H | 1 | 100 |
|   | 3 | 66.3 |
|   | 5 | 29.6 |
|   | 7 | 14.7 |
|   | 24 | 18.5 |
|   | 48 | 0 |

From these results, the formulations of the present invention are clearly able to repel lice. Furthermore, with the exception of formulation B, these formulations show a significant ability to repel lice for up to 48 hours after a single treatment. As noted previously, such a function of these formulations is useful for preventing an infestation of lice in a subject, particularly during an outbreak of lice in a group of subjects which may be in close physical contact, such as a group of school-age children. Thus, the formulations of the present invention are clearly useful to prevent an infestation of lice in a subject.

What is claimed is:

1. A composition for the treatment of lice, comprising:
    (a) anise oil being present at a concentration in a range of from about 5% to about 40% volume per volume;
    (b) isopropyl alcohol being present at a concentration in a range of from about 20% to about 60% volume per volume; and
    (c) at least one ingredient selected from the group consisting of fixed oil and emollient ester of fatty acid derived from vegetable oil, said at least one ingredient being present at a concentration in a range of from about 30% to about 50% volume per volume.

2. The composition of claim 1, wherein said fixed oil is selected from the group consisting of almond oil, avocado oil, maize oil, olive oil, peanut oil, soya oil, sunflower oil, sesame seed oil, coconut oil and safflower oil.

3. The composition of claim 2, wherein said fixed oil is fractionated coconut oil.

4. The composition of claim 1, wherein said alcohol is present in a concentration of from about 20% to about 40%.

5. The composition of claim 1, wherein said emollient ester of fatty acid derived from vegetable oil is selected from the group consisting of medium chain triglycerides (MCT), caprylic/capric triglycerides, isopropyl myristate, propylene glycol dicaprylate—dicaprate and isopropyl palmitate.

6. The composition of claim 1, further comprising rosemary oil.

7. The composition of claim 6, wherein said anise oil and said rosemary oil are each present at a concentration in a range of from about 5% to about 25% volume per volume.

8. The composition of claim 1, further comprising sassafras oil.

9. The composition of claim 8, wherein said sassafras oil is present at a concentration in a range of from about 5% to about 25% volume per volume.

10. The composition of claim 1, wherein said at least one ingredient selected from the group consisting of fixed oil and emollient ester of fatty acid derived from vegetable oil is olive oil.

11. A method for treatment of a subject against lice, comprising the step of topically applying a composition to the subject, the composition comprising:
    (a) anise oil being present at a concentration in a range of from about 5% to about 40% volume per volume;
    (b) isopropyl alcohol being present at a concentration in a range of from about 20% to about 60% volume per volume; and
    (c) at least one ingredient selected from the group consisting of fixed oil and emollient ester of fatty acid derived from vegetable oil, said at least one ingredient being present at a concentration in a range of from about 30% to about 50% volume per volume.

12. The method of claim 11, wherein said fixed oil is selected from the group consisting of almond oil, avocado oil, maize oil, olive oil, peanut oil, soya oil, sunflower oil, sesame seed oil, coconut oil and safflower oil.

13. The method of claim 12, wherein said fixed oil is coconut oil.

14. The method of claim 11, wherein said alcohol is present in a concentration of from about 20% to about 40%.

15. The method of claim 11, wherein said emollient ester of fatty acid derived from vegetable oil is selected from the group consisting of medium chain triglycerides (MCT), caprylic/capric triglycerides, isopropyl myristate, propylene glycol dicaprylate—dicaprate and isopropyl palmitate.

16. The method of claim 11, further comprising rosemary oil.

17. The method of claim 16, wherein said anise oil and said rosemary oil are each present at a concentration in a range of from about 5% to about 25% volume per volume.

18. The method of claim 11, further comprising sassafras oil.

19. The method of claim 18, wherein said sassafras oil is present at a concentration in a range of from about 5% to about 25% volume per volume.

20. The method of claim 11, wherein said at least one ingredient selected from the group consisting of fixed oil and emollient ester of fatty acid derived from vegetable oil is olive oil.

21. The method of claim 11, wherein the step of topically applying said composition to the subject is performed by applying said composition to hair and skin of the head of the subject.

22. The method of claim 21, wherein the treatment of the subject against lice includes killing an egg of the lice.

23. The method of claim 21, wherein the treatment of the subject against lice includes repelling lice from the head of the subject.

* * * * *